United States Patent
Gips et al.

(10) Patent No.: US 9,111,435 B2
(45) Date of Patent: Aug. 18, 2015

(54) REDUCING MEDICAL ERROR

(75) Inventors: Jonathan Peter Gips, Boston, MA (US); Philip Angus Liang, Peak (HK); Ryan Patrick Aylward, Boston, MA (US); Aaron Douglas Valade, Boston, MA (US)

(73) Assignee: SNIF Labs, Inc., Cambridge, MA (US)

( * ) Notice: Subject to any disclaimer, the term of this patent is extended or adjusted under 35 U.S.C. 154(b) by 732 days.

(21) Appl. No.: 12/756,811

(22) Filed: Apr. 8, 2010

(65) Prior Publication Data

US 2010/0262430 A1  Oct. 14, 2010

Related U.S. Application Data

(60) Provisional application No. 61/212,217, filed on Apr. 8, 2009.

(51) Int. Cl.
 *G08B 13/24* (2006.01)
 *G08B 21/24* (2006.01)
 *G06F 19/00* (2011.01)
 *G06Q 50/22* (2012.01)

(52) U.S. Cl.
 CPC .............. *G08B 21/24* (2013.01); *G06F 19/327* (2013.01); *G06Q 50/22* (2013.01); *G08B 21/245* (2013.01)

(58) Field of Classification Search
 None
 See application file for complete search history.

(56) References Cited

U.S. PATENT DOCUMENTS 5,886,634 A    3/1999  Muhme
7,158,030 B2 *  1/2007  Chung ................ 340/572.1
2004/0090333 A1  5/2004  Wildman et al.
2005/0062603 A1  3/2005  Fuerst et al.
2006/0006999 A1 * 1/2006  Walczyk et al. ........ 340/539.27
2007/0229288 A1 * 10/2007  Ogrin et al. ............. 340/573.1

FOREIGN PATENT DOCUMENTS

EP    1872802 A1    1/2008
EP    1913892 A2    4/2008

OTHER PUBLICATIONS

International Preliminary Report on Patentability, mailed Oct. 20, 2011, received in counterpart International Patent Application No. PCT/US2010/030411, 7 pgs.

International Search Report with Written Opinion, dated Jun. 9, 2010, received in international patent application No. PCT/US10/30411, 9 pgs.

"Chinese Application Serial No. 201080025263.8, Office Action mailed Apr. 25, 2013", 14 pgs.

"Chinese Application Serial No. 201080025263.8, Response filed Nov. 8, 2013 to Office Action mailed Apr. 25, 2013", 15 pgs.

"European Application Serial No. 10762444.7, Extended Search Report mailed Sep. 6, 2012", 7 pgs.

"European Application Serial No. 10762444.7, Examination Notification Art. 94(3) mailed May 7, 2013", 6 pgs.

(Continued)

*Primary Examiner* — Michelle L Le
(74) *Attorney, Agent, or Firm* — Schwegman Lundberg & Woessner, P.A.

(57) ABSTRACT

A method, apparatus, and system for reducing medical error may comprise receiving an enter signal including an enter status when a first worker device enters a zone. An exit signal including an exit status may be received when the first worker device exits the zone. Moreover an action signal including an action status may be received if an action device is actuated.

28 Claims, 12 Drawing Sheets

(56) References Cited

OTHER PUBLICATIONS

Heller, A., et al., "Amperometric Biosensors Based on Three-Dimensional Hydrogel-Forming Epoxy Networks", Sensors and Actuators B, 13(1-3), (May 1993), 180-183.

Heller, A., "Plugging metal connectors into enzymes", Nat Biotechnol., 21(6), (Jun. 2003), 631-2.

Hicks, J. M, "In Situ Monitoring", Clin. Chem., 31(12), (Dec. 1985), 1931-1935.

Hitchman, M. L, et al., "Measurement of Dissolved Oxygen: Chapter 3: Principles of Voltammetry", Chemical Analysis, vol. 49, (1978), 34-123.

Hrapovic, S., et al., "Picoamperometric Detection of Glucose at Ultrasmall Platinum-Based Biosensors: Preparation and Characterization", Analytical Chemistry, 75(14), (2003), 3308-3315.

Hu, Y., et al., "A Needle-type enzyme-based lactate sensor for in vivo monitoring", Analytica Chimica Acta, 281(3), (Sep. 24, 1993), 503-511.

Huang, C. J, et al., "Electrochemical Generation of Oxygen", Electrochemistry Research laboratory, (1972), 1-115.

Hunter, I. Jones, et al., "Minimally Invasive Glucose Sensor and Insulin Delivery System", MIT Home Automation and Healthcare Consortium Progress Report No. 25, (2000).

Ianniello, R. M, et al., "Differential Pulse Voltammetric Study of Direct Electron Transfer in Glucose Oxidase Chemically Modified Graphite Electrodes", Analytical Chemistry, 54(7), (1982), 1098-1101.

Ianniello, R. M, et al., "Immobilized Enzyme Chemically Modified Electrode as an Amperometric Sensor", Analytical Chemistry, 53(13), (1981), 2090-2095.

Ikeda, T., et al., "Glucose Oxidase-Immobilized Benzoquinone-Carbon Paste Electrode as a Glucose Sensor", Agricultural and Biological Chemistry, vol. 49, No. 2, (1985), 541-543.

Ikeda, T., et al., "Kinetics of Outer-Sphere Electron Transfers Between Metal Complexes in Solutions and Polymeric Films on Modified Electrodes", Journal of the American Chemical Society, 103(25), (1981), 7422-7425.

"Chinese Application Serial No. 201080025263.8, Office Action mailed Mar. 18, 2014", 15 pgs.

"European Application Serial No. 10762444.7, Summons to Attend Oral Proceedings mailed Dec. 18, 2014", 6 pgs.

* cited by examiner

| 502 — Enter Status | |
|---|---|
| Date | 12/13/2009 — 504 |
| Time | 05:22:34 PM — 506 |
| Zone ID | Patient Room 136 — 508 |
| Compliance Device ID | 00000081 — 510 |

| 512 — Exit Status | |
|---|---|
| Date | 12/13/2009 — 514 |
| Time | 05:28:12 PM — 516 |
| Zone ID | Patient Room 136 — 518 |
| Compliance Device ID | 00000081 — 520 |

| 522 — Action Status | |
|---|---|
| Date | 12/13/2009 — 524 |
| Time | 05:28:46 PM — 526 |
| Zone ID | Patient Room 136 — 528 |
| Activity Device ID | 00000153 — 530 |

FIG. 5

| Observed Activities – Worker Device 404 – 12/13/2009 |||||
| --- | --- | --- | --- | --- |
| | Patient Room 136 || Laboratory 107 ||
| | Enter | Exit | Enter | Exit |
| Indication | 05:22:34 PM | 05:28:12 PM | 06:15:00 PM | 06:17:23 PM |
| Compliance Opportunity | 602 — + | | 606 — + | |
| Compliance Action | 604 — 05:28:46 PM | | - | |
| Adherence Rate | 608 — 50% ||||

FIG. 6a

| Signal/Detection ||||||
| --- | --- | --- | --- | --- | --- |
| Location – Patient Room 136 | Strength | Threshold Strength | Timer Length | Timer Current | Exit |
| Enter Signal | 0 dBM | -1 dBM | 120 s | 0 s | exit |
| Action Signal | 1 dBM | 0 dBM | | | |

FIG. 6b

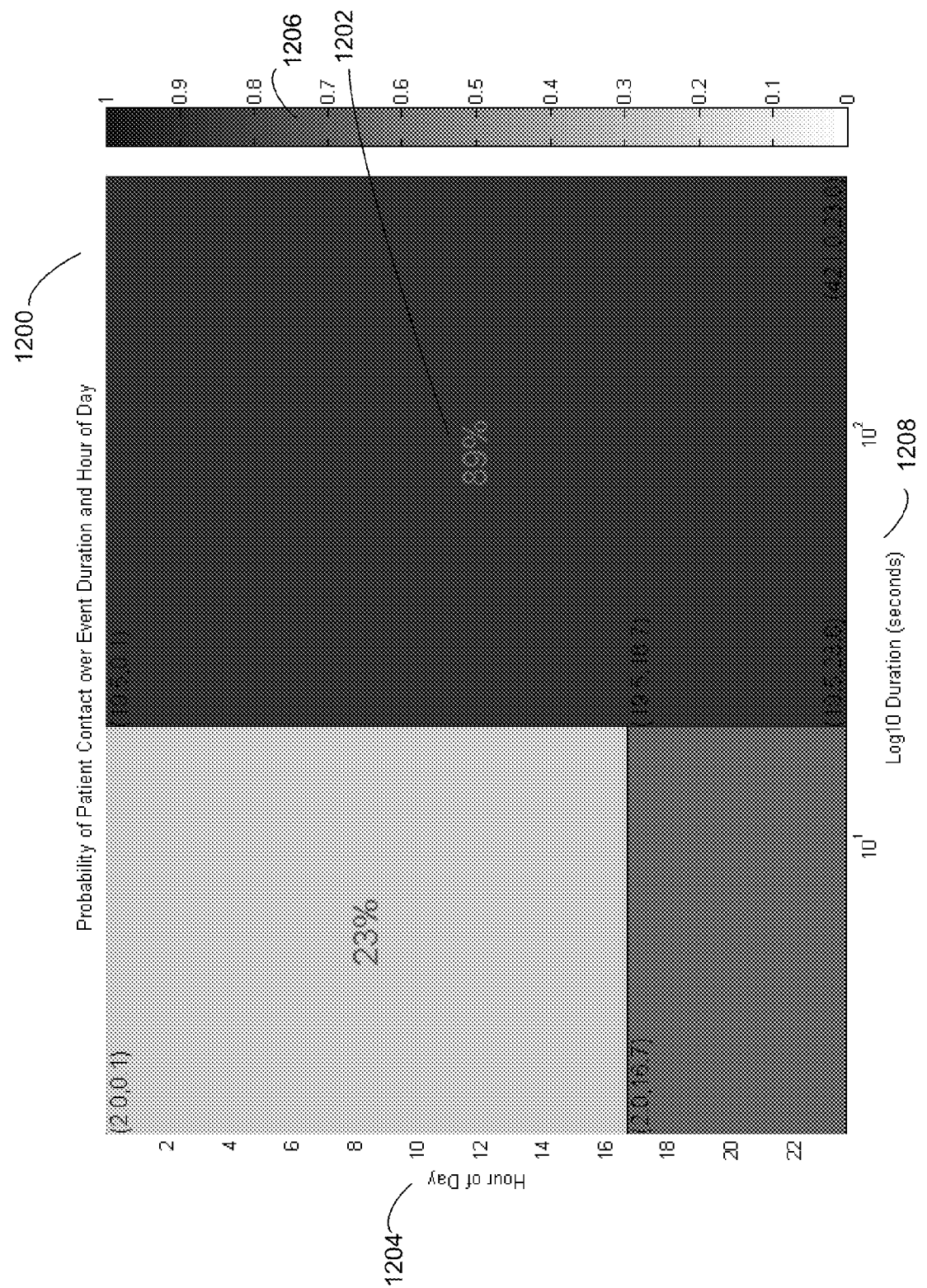

REDUCING MEDICAL ERROR

RELATED APPLICATIONS

This application claims the benefit of U.S. Provisional Patent Application No. 61/212,217 filed on 8 Apr. 2009, the entire contents of which are herein incorporated by reference.

BACKGROUND OF THE INVENTION

This disclosure relates to reducing medical error and, more particularly, to a method, apparatus, and system for reducing medical error.

Medical error may cause health-care associated infections. Infection prevention practices may reduce medical error and thereby may reduce health-care associated infections. Sometimes infection prevention practices may not be adhered to. Further, it may be difficult to measure adherence rates of compliance with infection prevention practices.

Some health-care organizations may not measure compliance with infection prevention practices at all. Other health-care organizations that may measure compliance with infection prevention practices may do so by visual observation methods. Visual observation methods may be time-consuming, subjective, and/or may create feelings of mistrust between coworkers. Accordingly, there may be a need to measure compliance with infection prevention practices that may reduce dependence on visual observation methods.

BRIEF SUMMARY OF THE INVENTION

In a first embodiment, a method for reducing medical error may comprise receiving an enter signal including an enter status when a first worker device enters a zone. The method may further comprise receiving an exit signal including an exit status when the first worker device exits the zone. Additionally, the method may comprise receiving an action signal including an action status if an action device is actuated.

One or more of the following features may be included. The presence of at least one of a compliance opportunity and a compliance action, based upon, at least in part, at least one of the enter status, the exit status, and the action status may be determined. At least one of the enter status, the exit status, and the action status may be sent to a server computer. A proximity between the first worker device and at least one of a compliance device and a second worker device may be calculated. The zone may be determined based upon, at least in part, the proximity. An adherence rate based upon, at least in part, the at least one compliance opportunity and compliance action may be calculated.

In some implementations, at least one of the enter status, the exit status, and the action status may include at least one of a date and time, a zone identification, an action device identification, and a compliance device identification. At least one of the compliance opportunity and compliance action may be determined based upon, at least one of the date and time, the zone identification, the action device identification, and the compliance device identification.

The method may further comprise aggregating a plurality of enter statuses, exit statuses, and action statuses into a time-based sequence of events. The method may also comprise running the sequence through at least one predefined rule. The presence of at least one of a compliance opportunity and compliance action may be determined based upon, at least in part, the sequence and the at least one predefined rule.

An adherence rate may be calculated based upon, at least in part, the at least one compliance opportunity and compliance action.

In a second embodiment, an apparatus for reducing medical error may comprise a first worker device configured to receive an enter signal including an enter status when the first worker device enters a zone, an exit signal including an exit status when the first worker device exits the zone, and an action signal including an action status if an action device is actuated. One or more of the following features may be included. The apparatus may further comprise a computing device configured to determine the presence of at least one of a compliance opportunity and a compliance action, based upon, at least in part, at least one of the enter status, the exit status, and the action status. The first worker device may be further configured to send at least one of the enter status, the exit status, and the action status to a server computer. The first worker device may be further configured to calculate a proximity between the first worker device and at least one of a compliance device and a second worker device. The first worker device may also be configured to determine the zone based upon, at least in part, the proximity.

In a third embodiment, a system for reducing medical error may comprise a first worker device configured to receive an enter signal including an enter status when the first worker device enters a zone, an exit signal including an exit status when the first worker device exits the zone, and an action signal including an action status if an action device is actuated. The action device may be configured to transmit the action signal including the action status if the action device is actuated.

One or more of the following features may be included. A compliance device may be configured to transmit the enter signal including the enter status when the first worker device enters the zone, and transmit the exit signal including the exit status when the first worker device exits the zone. A server computer may be configured to receive at least one of the enter status, the exit status, and the action status. At least one of the first worker device, the action device, compliance device, and the server computer may be configured to determine the presence of at least one of a compliance opportunity and a compliance action, based upon, at least in part, at least one of the enter status, the exit status, and the action status. At least one of the first worker device, the action device, compliance device, and the server computer may be configured to calculate an adherence rate based upon, at least in part, the at least one compliance opportunity and compliance action.

In some implementations, at least one of the first worker device and the compliance device may be further configured to calculate a proximity between the first worker device and the compliance device, and determine the zone based upon, at least in part, the proximity. The system may further comprise a second worker device, wherein at least one of the first worker device and the second worker device may be further configured to calculate a proximity between the first worker device and the second worker device, and determine the zone based upon, at least in part, the proximity. At least one of the enter status, the exit status, and the action status may include at least one of a date and time, a zone identification, an action device identification, and a compliance device identification.

At least one of the first worker device, the action device, compliance device, and the server computer of the system may be configured to aggregate a plurality of enter statuses, action statuses, and exit statuses into a time-based sequence of events, and run the sequence through at least one predefined rule. The presence of the at least one of a compliance opportunity and compliance action based upon, at least in part, the sequence and the at least one predefined rule may be determined. An adherence rate based upon, at least in part, the at least one compliance opportunity and compliance action may be calculated.

In a fourth embodiment, a hand hygiene system for reducing medical error may comprise a beacon device in a patient zone configured to transmit an enter signal including an enter status when a body-worn device enters the patient zone, and an exit signal including an exit status when the body-worn device exits the patient zone. The system may further comprise a dispense device configured to transmit a dispense signal including a dispense status if the dispense device is actuated. The body-worn device may be configured to receive the enter signal including the enter status when the body-worn device enters the patient zone, the dispense signal including the dispense status if the dispense device is actuated, and the exit signal including the exit status when the body-worn device exits the patient zone.

In a fifth embodiment, a method for reducing medical error may comprise detecting an enter event when a monitoring device receives an enter signal with at least an entrance threshold signal strength associated with a zone. The method may further comprise setting a timer associated with the zone. The method may also comprise, if an action device is actuated, detecting an action event when the monitoring device receives an action signal with at least an action threshold signal strength. Additionally, the method may comprise detecting an exit event when the timer expires.

One or more of the following features may be included. The presence of at least one of a compliance opportunity and a compliance action may be determined, based upon, at least in part, at least one of the enter event, the exit event, and the action event. An adherence rate may be calculated, based upon, at least in part, the at least one compliance opportunity and compliance action. The compliance opportunity may be determined based upon, at least in part, a probability of contact. The probability of contact may be retrieved from a lookup table.

BRIEF DESCRIPTION OF THE SEVERAL VIEWS OF THE DRAWINGS

FIG. 5 is a series of tables showing information which may be sent between devices during the medical error reduction process;

FIG. 6a is a table showing calculation of an adherence rate for medical error reduction;

FIG. 6b is a table showing detection of events used to calculate an adherence rate for medical error reduction;

FIG. 11 is a table associated with an embodiment of the medical error reduction process.

DETAILED DESCRIPTION OF THE INVENTION

Figure 1:
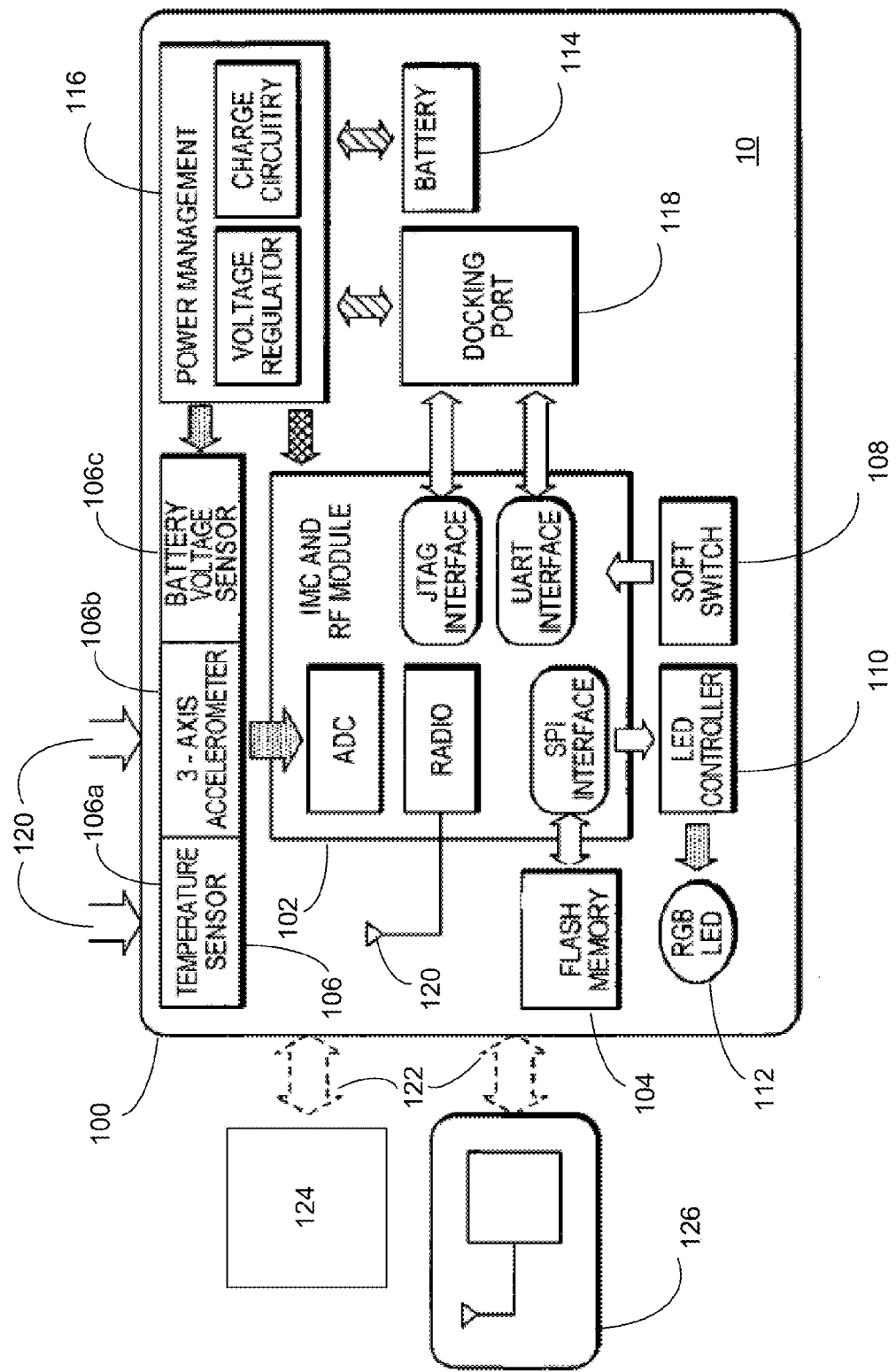
FIG. 1 is a diagrammatic view of a monitoring system and/or device.
Figure 2:
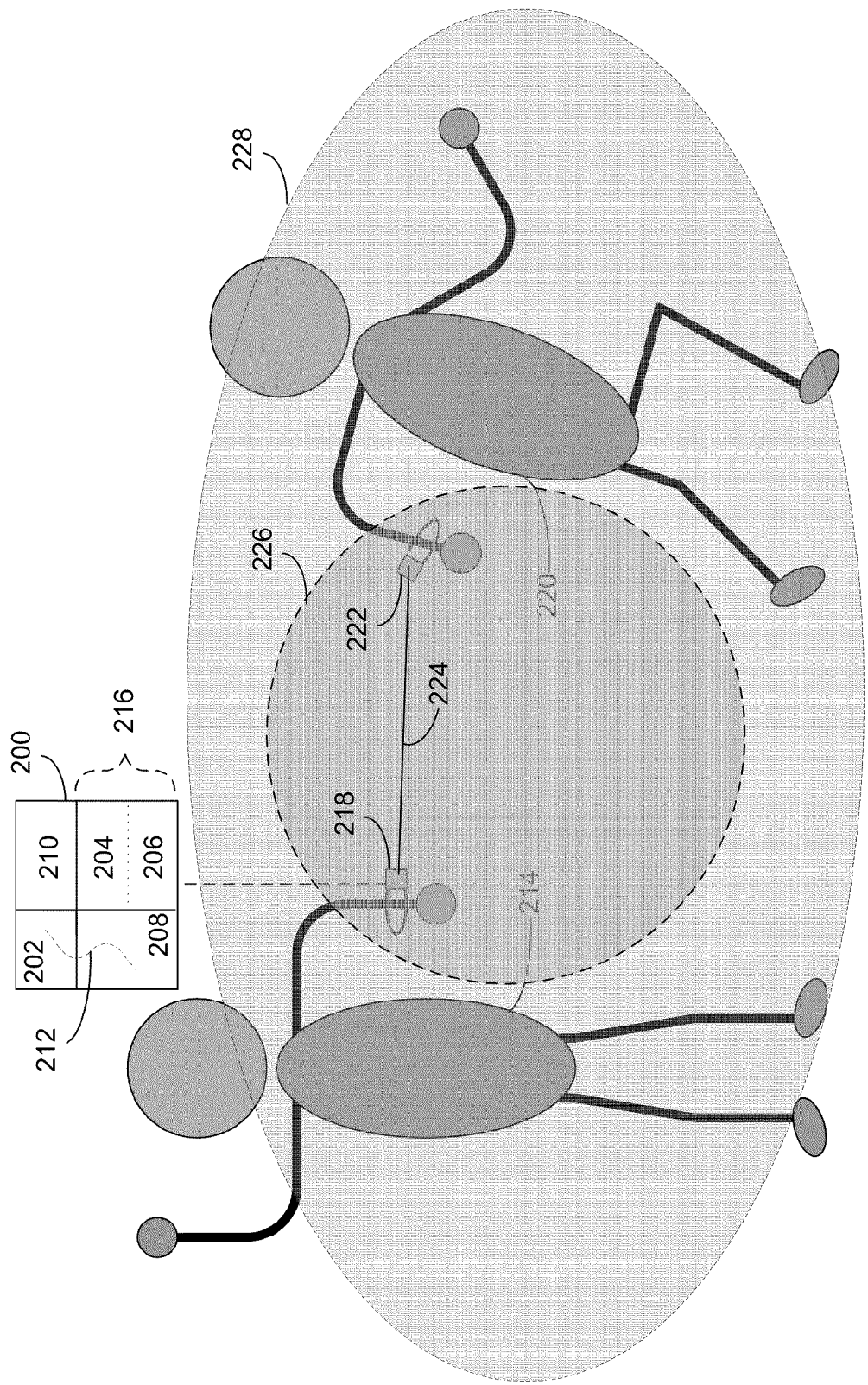
FIG. 2 is a diagrammatic view of one implementation of a medical error reduction process.

Referring to FIGS. 1 & 2, there is shown a monitoring device 10. Monitoring device 10 is merely an example of a system and/or device which may be configured to operate in accordance with the subject application. Monitoring device 10 may be an electronic tag which may be attached to an object or worn by a person (e.g., humans 214 and 220). Monitoring device 10 may comprise several components housed in an enclosure (e.g., enclosure 100). Enclosure 100 may be of a compact form that may be attached to an object (e.g., humans 214 and 220). Enclosure 100 may be fixed to a collar, necklace, bracelet, or other wearable accessory. In such a case, enclosure 100 may take the form of a conventional tag, such as an ID tag or badge worn by an employee at a workplace (e.g., a hospital). Monitoring device 10 may include an integrated microcontroller (IMC) and radio frequency (RF) module 102, flash memory storage 104, a plurality of sensors 106, soft switch 108, light emitting diode (LED) controller 110 which may control an LED 112, battery 114, power management circuitry 116 and docking port 118. In one embodiment, as shown in FIG. 2, an RF module (e.g., RF module 216) may be separate from an IMC and may include receiver 204 and transmitter 206.

Additionally, plurality of sensors 106 may include temperature sensor 106a and accelerometer 106b, which may measure environmental conditions relative to monitoring device 10. One or more of plurality of sensors 106 may measure one or more characteristics of an object that monitoring device 10 may be attached to. For example, temperature sensor 106a may receive environmental input 120, and may be adapted to detect the ambient air temperature of the environment or the temperature of a nearby surface, such as the surface of the object attached to monitoring system 10. Again by example, accelerometer 106b may be a 3-axis accelerometer which may detect acceleration, deceleration and other movements of the monitoring system 10 and/or the object it may be attached to. Accelerometer 106b may utilize four analog outputs to provide measurements in real time to IMC module 102. Alternatively, other sensors may be substituted for or added to plurality of sensors 106, thereby providing other measurements relating to the environment or the object. For example, alternative sensors may measure audio (e.g., human speech), ambient light, humidity, altitude, or heart rate of the object (e.g., a person).

IMC module 102 may perform a number of functions as determined by the mode of operation of monitoring device 10. IMC 102 may receive analog signals from plurality of sensors 106, and may convert the signals to digital signals with an analog-to-digital converter (ADC). Further, IMC 102 may capture and process the signals according to one or more software or firmware programs stored at IMC 102 or flash memory 104. The signals may be processed at IMC 102, for example, by sampling the signals at variable intervals, deriving a conditioned selection of signals, detecting an event based on the signals, or producing data relating to a set of signals. The processed event data may be stored to flash memory 104 through a serial peripheral interface (SPI). The event data may also be sent to the radio (RF) module (at IMC 102) with antenna 120, where it may be transmitted via wireless communication 122 to computer 124 or remote device 126. Computer 124 may be a server computer, base station, access point, personal computer, or other system. Remote device 126 may be a similar device to monitoring device 10, and may include any of the features of monitoring system 10. The RF module at IMC 102 may also receive wireless signals from computer 124 or one or more remote devices (e.g., remote device 126), enabling data transfer or other communication.

For example, one mode of operation of monitoring device 10 and/or remote device 126 may be discovery mode and/or ping mode. While in discovery mode and/or ping mode, monitoring device 10 and/or remote device 126 may be configured to operate in accordance with a discovery protocol as described in U.S. patent application Ser. No. 12/553,921, which is incorporated herein by reference. Monitoring device 10 and/or remote device 126 may also use other communication methods and/or protocols.

In some embodiments, computer 124 may be a wall or USB-powered base station connected to a network over Ethernet, WiFi, WiMax, GSM, or through USB to a computer that itself may be connected to the network. The base station may be an access point for the tag and may be centrally located in, for example, a hospital, and may allow the tag to transfer information to and from a computer server on the network. Information transferred may include, but is not limited to, tag firmware updates, data stored in flash memory 104, real-time status messages, status information, and device settings.

IMC 102 may be programmed to detect a particular reading or signal. The reading or signal may signify an "event", which may be received from one or more of the plurality of sensors 106, from communication with computer 124, or communication with a remote device (e.g., remote device 126). In response to the event, IMC 102 may send a signal to LED controller 110, which may indicate to activate one or more LED lights 112. LED lights 112 may turn on or enter a blinking pattern to indicate the occurrence of the event. For example, one or more LED lights 112 may flash to indicate that battery 114 is low on power, flash memory 104 is full, the ambient temperature has reached a threshold, or another device (e.g., remote device 126) is nearby.

Further, soft switch 108 may connect to IMC 102 and may be configured to toggle modes of operation of monitoring device 10, such as power on, power off and low power operation. IMC 102 may also interface with docking port 118, which may connect to a port of a base station. Through this link, IMC 120 may transfer data stored at flash memory 104, as well as information about monitoring device 10 such as hardware and software settings, storage capacity, and firmware version. IMC 102 may also receive commands and data from the base station, such as a command to update firmware of IMC 102, accompanied by updated firmware.

As discussed above, in some embodiments, the RF module may be separate from IMC 102. As shown in FIG. 2, RF module 216 may include receiver 204 and transmitter 206, both of which may be included in the monitoring device (e.g., worker device 200). Receiver 204 and transmitter 206 may transmit and receive infrared signals, visible light signals, acoustic signals, or data modulated in other mediums. When transmitting and receiving RF signals, the monitoring device (e.g., worker device 200) may be in RF mode. In RF mode, receiver 204 and transmitter 206 may be configured to transmit and receive RF signals. However, the monitoring device (e.g., worker device 200) may switch to other modes in order to communicate (i.e., transmit and receive) using Bluetooth, Zigbee, WiFi (802.11), and/or infrared (IR) signals.

Discovery mode and/or ping mode may allow each device (e.g., monitoring device 10 and/or remote device 126) in an environment to maintain up-to-date knowledge about the presence of other devices. The environment may be an area in which there are multiple devices (e.g. monitoring device 10 and/or remote device 126) that are discoverable to one another. The environment may also be referred to as a network.

Further, discovery mode and/or ping mode may be optimized such that real-time activity classification may be used to dynamically adjust ping periods. The average ping period for each discoverable device in the network may be maximized, while reliable device discovery may be maintained. In other words, shorter ping periods (i.e., faster ping rates) may be necessary when devices are in a state of motion. This may cause frequent changes to the network structure (i.e., ping periods of each device) in the environment. Ping periods of devices (e.g., monitoring device 10 and/or remote device 126) may be adjusted using an activity state classification as described in U.S. patent application Ser. No. 12/553,900, which is incorporated herein by reference.

Worker device 200 may be similar to monitoring device 10 and/or remote device 126 and may include any of the features thereof. Worker device 200 may be a tag or badge worn by a human such as a nurse, for example. Worker device 200 may be worn as a bracelet around the wrist (e.g., bracelets 218 and 220), as a necklace around the neck, or may be otherwise attached to a human (e.g., humans 214 and 220). For exemplary purposes, worker device 200 is shown as being worn as a bracelet by human 214. Similar to monitoring system 10, worker device 200 may include one or more sensors (e.g., sensor 202), a receiver (e.g. receiver 204), a transmitter (e.g., transmitter 206), a controller (e.g., controller 208) and a battery (e.g., battery 610). Controller 208 may be similar to IMC 102 of monitoring device 10. In some embodiments, controller 208 may be any type of microcontroller, microprocessor, or processor configured to perform the operations described herein. Further, receiver 204 and transmitter 206 may be included in a single module, such as a transceiver or RF module. Similarly, receiver 204, transmitter 206, and controller 608 may be part of the same module, such as IMC/RF module 102 of monitoring device 10.

For example, monitoring device 10 may receive a signal from a beacon device or worker device 200 when in discovery and/or ping mode. The beacon device may transmit the signal, which may be a periodic signal. The signal may be a ping, which may be a burst of short RF packets. The ping may include status information such as a date, time, zone ID (i.e., location), and/or a compliance device ID that may be associated with the beacon device, as shown in, for example, enter status 502 of FIG. 5. Multiple beacon devices may be placed throughout an environment, such as a hospital, and may be logically connected to create complex zones.

Further, monitoring device 10 may measure a signal strength of the signal, or a received signal strength indication (RSSI). The RSSI may be measured in dBm, or the power ratio in decibels (dB) of the measured power referenced to one milliwatt. Monitoring device 10 may apply an event detection algorithm to the RSSI in order to detect events. For example, if monitoring device 10 receives a signal with an RSSI above a certain threshold, monitoring device 10 may detect an event. Further by way of example, if a nurse wearing monitoring device 10 walks into a patient room with an RSSI threshold of −1 dBm associated with it, and monitoring device 10 receives a signal with an RSSI of 0 dBm from a beacon device in the patient room, monitoring device 10 may detect an enter event (i.e., monitoring device 10 has entered the patient room). In this way, monitoring device 10 may detect a variety of events including but not limited to enter events (e.g., when monitoring device 10 has entered a location), exit events (e.g., when monitoring device 10 has exited a location) and/or action events (e.g., monitoring device 10 detects that an action device, such as a soap dispenser, has been actuated).

As discussed above, Worker device 200 may be a tag, badge, strip, insert, etc. (e.g., an ID tag) worn by a human (e.g., a worker in a building or a nurse in a hospital). In other words, worker device 200 may be a body-worn device. For example, if worker device 200 is an ID tag worn by a nurse in a hospital, worker device 200 may be in communication with a base station located in the hospital. Worker device 200 may relay information describing the nurse's movement around the hospital to the base station. Further, worker device 200 may be in communication with other devices in the hospital (e.g., other worker devices, beacon devices, monitoring devices, and/or remote devices), and may discover such devices in accordance with a discovery protocol, as discussed above. Worker device 200 may be rechargeable and may be charged with, for example, a badge charger. The badge charger may be a 16-unit charger and may charge a badge (e.g., a worker device) in a few hours. Worker device 200 may be stored and/or recharged in the badge charger between an employee's (e.g., a nurse) shifts.

In another embodiment, a first worker device (e.g., worker device 200) worn by a first nurse (e.g., bracelet 218 worn by human 214) may receive signals from a second worker device worn by a second nurse (e.g., bracelet 222 worn by human 214). These signals may be processed by controller 208 to produce event data. The event data may relate to the environment and the behavior of the nurse, such as his/her activities (e.g., whether he/she is walking, running, or at rest) and/or his/her interaction with other people wearing worker devices (e.g., remote devices), as may be evidenced by signals received from other worker devices. The event data may be transferred to a computing device (e.g., computer 124) in real time, or may be stored to a memory (e.g., flash memory 104) for transfer at a later time. Computer 124 may report the event data or transfer the data to a computer server via a network, or may analyze the data itself. The event data may be accessed (by, for example, an administrator) in order to monitor the behavior of people wearing worker devices (e.g., nurses). Worker device 200 may provide various alerts based upon, at least in part, the nurse's movement around the hospital or in relation to the other devices.

The devices (e.g., worker device 200) may communicate (e.g., transmit and receive) point-to-point information about their state. These devices may communicate without a system controller to centrally synchronize each device in the network. In other words, the devices in the network (e.g., worker device 200) may not require a central device for synchronization of each device in the network. In this way, a plurality of worker devices in a network may store a time-based log of information included in communications between each device.

Various client electronic devices may be directly or indirectly coupled to the network. For example, personal computers may be directly coupled to the network via a hardwired network connection. Notebook computers may be directly coupled to the network via a hardwired network connection. Laptop computers may be wirelessly coupled to the network via a wireless communication channel established between the laptop computer and a wireless access point (i.e., WAP), which may be directly coupled to the network. The WAP may be, for example, an IEEE 802.11a, 802.11b, 802.11g, Wi-Fi, and/or Bluetooth device that is capable of establishing wireless communication channel between a laptop computer and the WAP. A personal digital assistant may be wirelessly coupled the network via wireless communication channel established between the personal digital assistant and a cellular network/bridge, which may be directly coupled the network.

As is known in the art, all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows e.g., mobile phones, computers, and personal digital assistants to be interconnected using a short-range wireless connection.

Reducing Medical Error

Figure 3:
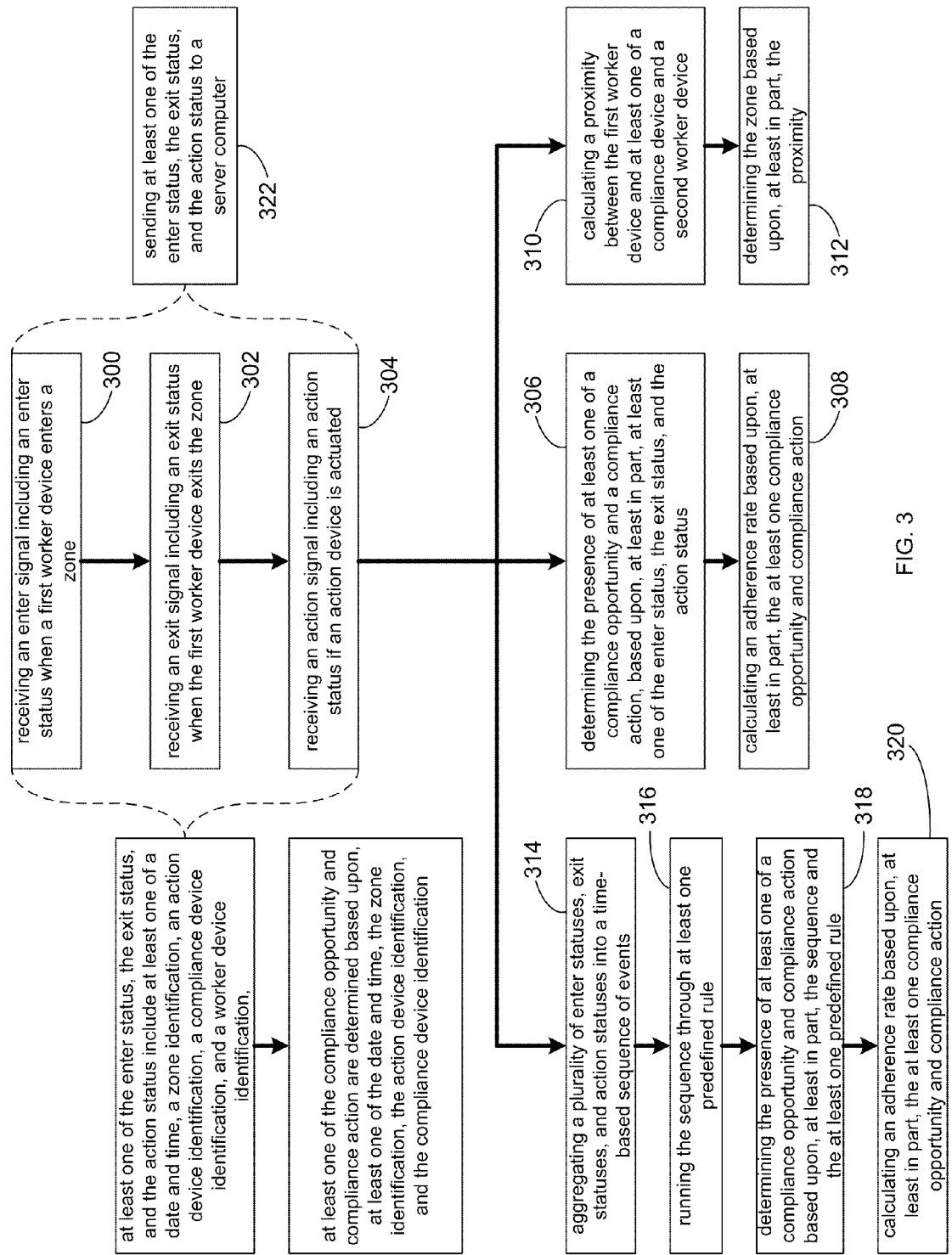
FIG. 3 is a flowchart of the medical error reduction process.
Figure 4A:
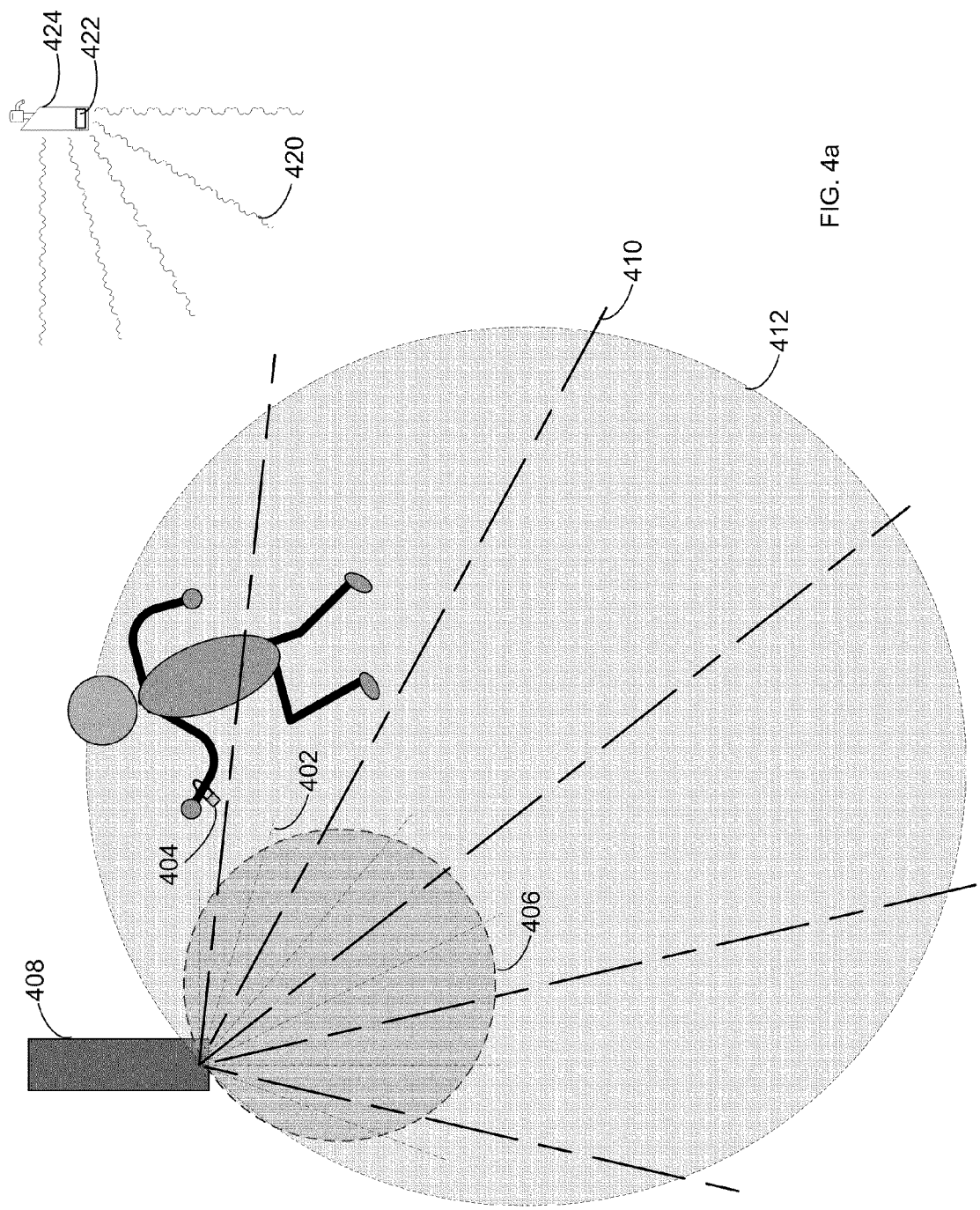
FIG. 4a is a diagrammatic view of one implementation of the medical error reduction process of FIG. 3.
Figure 4B:
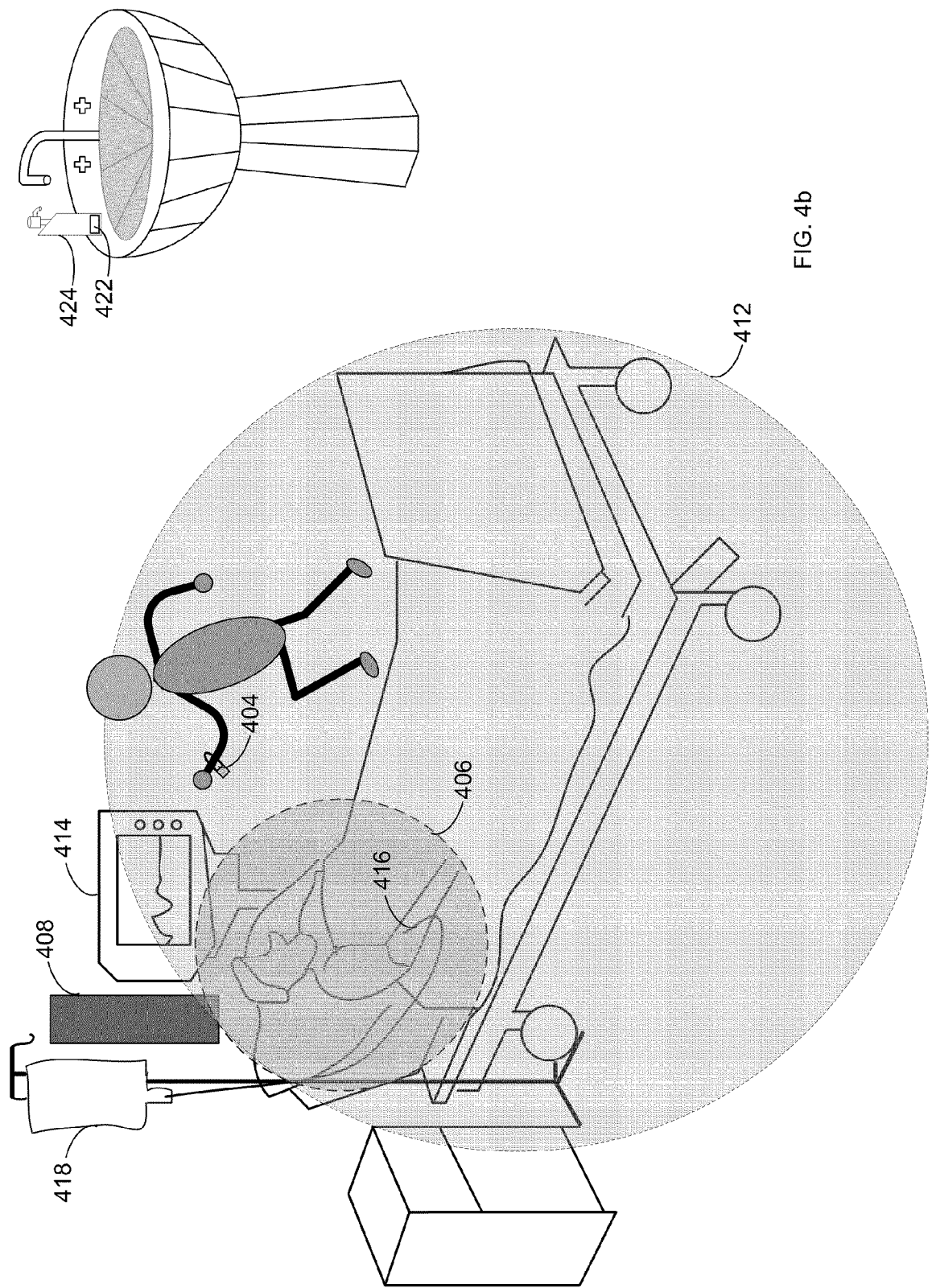
FIG. 4b is a diagrammatic view of one implementation of the medical error reduction process of FIG. 3.

Referring now to FIGS. 3 & 4, examples of reducing medical error will be described. For illustrative purposes only, FIGS. 4a & 4b show a hospital room configured to reduce medical error in accordance with the present disclosure. It should be noted, however, that the subject matter of the present disclosure may be applied to other areas besides hospital rooms, including but not limited to surgical preparation areas, laboratories, and bathrooms. As shown in FIGS. 3 & 4, an enter signal (e.g., signal 402) may be received 300 when a first worker device (e.g., worker device 404) enters a zone (e.g., entrance zone 406). Worker device 404 is shown as being affixed to a bracelet in FIGS. 4a & 4b for exemplary purposes only. Enter signal 402 may be received by worker device 404 and may include an enter status. Further, enter signal 402 may be sent by compliance device 408. Compliance device 408 may be a beacon device and may be placed near a patient bed in a hospital room. Worker device 404 may detect proximity to beacon devices. Compliance device 408 may be configured to transmit enter signal 402 when worker device 404 enters entrance zone 406.

The terms "enter signal", "exit signal", and "action signal" may be used throughout this disclosure to describe signals received and/or sent by a monitoring device (e.g., worker device 404). As described above, these signals may be pings and may have an associated RSSI. An "enter signal" may be a ping received by a monitoring device at or close to the time the monitoring device determines it has entered a zone, based on an RSSI threshold of the zone, for example. Similarly, an "exit signal" may be a ping received by the monitoring device at or close to the time the monitoring device determines it has exited a zone, based on the RSSI threshold of the zone, or the expiration of a timer set when an enter event is detected, for example. An "action signal" may be a ping received by the monitoring device at or close to the time the monitoring device determines an action has taken place, based on the RSSI threshold of an action device that is actuated, for example.

The terms "enter event", "exit event", and "action event" may be used throughout this disclosure to describe events detected by a monitoring device. An "enter event" may be detected by a monitoring device (e.g., worker device 404) when a signal with a signal strength of at least an RSSI threshold associated with a zone is received. An "exit signal" may be detected by a monitoring device (e.g., worker device 404) when a signal with a signal strength less than or equal to an RSSI threshold associated with a zone is received, or when a timer expires, for example. An "action event" may be detected by a monitoring device (e.g., worker device 404) when a signal with a signal strength of at least an RSSI threshold associated with an action device (e.g., a soap dispenser which transmits a signal when actuated) is received.

The terms "enter status", "exit status", and "action status" may be used throughout this disclosure to describe information received and/or sent with an enter signal, exit signal, or action signal, respectively. The terms "enter status", "exit status", and "action status" may each refer to information included in an RF packet included within a ping received by a monitoring device (e.g., worker device 404), including, but not limited to, the information shown in FIG. 5.

Entrance zone 406 may be, for example, an area around a patient, or a "patient zone". It may also be any area that may require an employee (e.g., a nurse) to wash his/her hands or perform another medical error reduction activity after entering the zone. Examples of other medical error reduction activities include, but are not limited to, changing hospital bed sheets, putting on gloves, masks, and/or hairnets, cleaning a medical care apparatus, and servicing a medical care device. Entrance zone 406 may also be adjustable. In one implementation, entrance zone 406 may be an area where patient contact may take place when entered.

Figure 10:
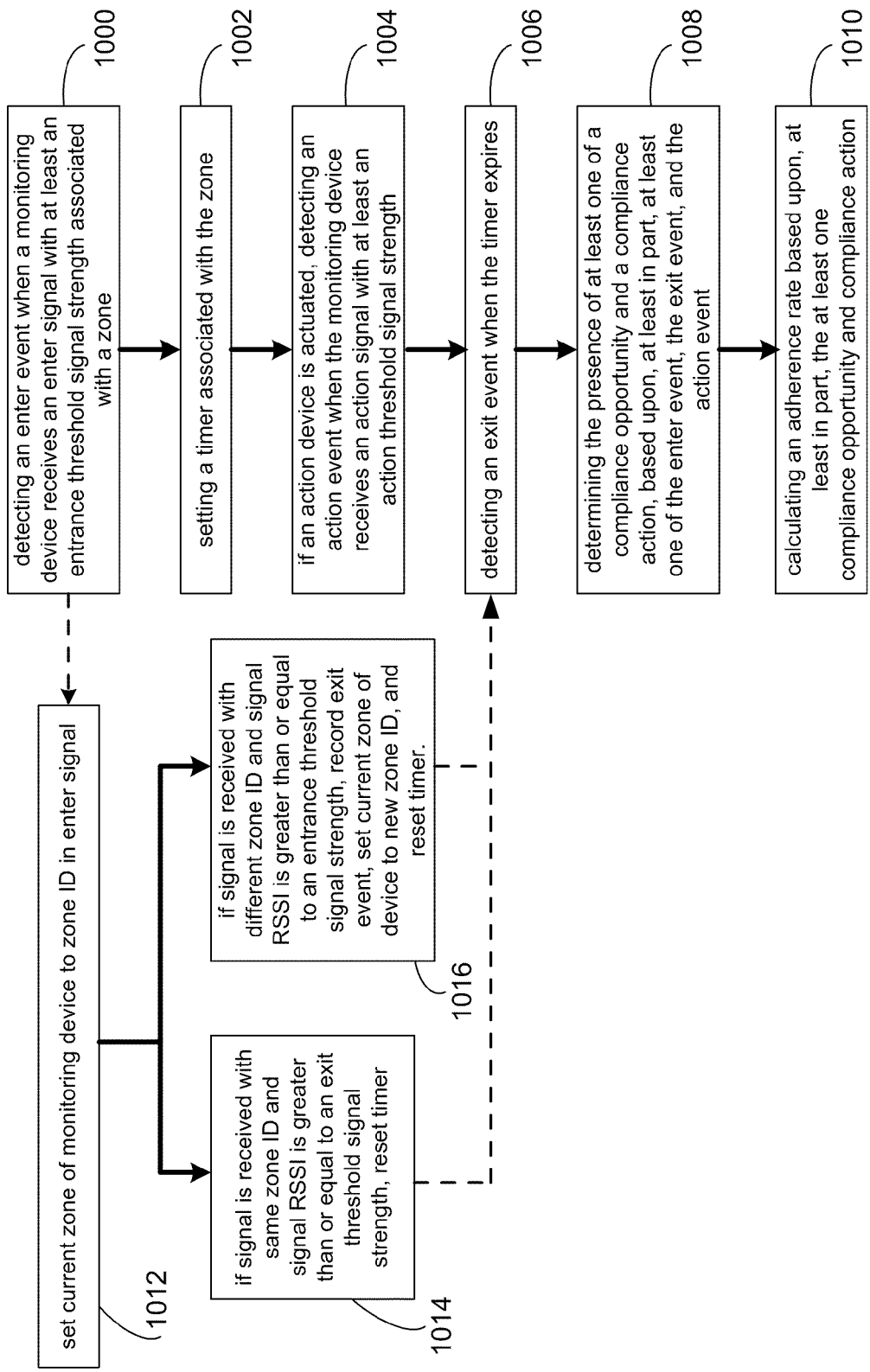
FIG. 10 is a flowchart of another embodiment of the medical error reduction process.

Referring now also to FIGS. 6b & 10, enter event 610 may be detected 1000 when a monitoring device (e.g., worker device 404) receives an enter signal (e.g., enter signal 612) with at least an entrance threshold signal strength (e.g., entrance threshold signal strength 614) associated with a zone (e.g., entrance zone 406). Entrance threshold signal strength 614 may be associated with the zone (e.g., entrance zone 406). In other words, when enter event 610 is detected, the monitoring device (e.g., worker device 404) may be within the zone (e.g., entrance zone 406). The monitoring device may apply an event detection algorithm to compare the signal strength (RSSI) of enter signal 612 with entrance threshold signal strength 614. Further, the monitoring device (e.g., worker device 404) may set 1002 timer 616 which may be associated with the zone (e.g., entrance zone 406). Timer 616 may be set once enter event 610 is detected. When timer 616 is set, it may begin to count down an adjustable period of time (e.g., 120 s as shown in FIG. 6b). The adjustable period of time may represent an amount of time an employee (e.g., a nurse) in a hospital may need to be in a patient room. In this way, the monitoring device (e.g., worker device 404) may detect 1006 exit event 624 when timer 616 expires. The monitoring device (e.g., worker device 404) may store enter event 610 and/or exit event 624 in its memory (e.g., flash memory 104) and/or may send an indication of enter event 610 and/or exit event 624 to computer 124.

Continuing with the previous example, an exit signal (e.g., signal 410) may be received 302 when first worker device 404 exits entrance zone 406. Exit signal 410 may be received by worker device 404 and may include an exit status. Further, exit signal 410 may be sent by compliance device 408. Exit signal 410 may have an RSSI less than or equal to entrance threshold signal strength 614 associated with entrance zone 406. After an enter signal is received, and an exit signal is then received with an RSSI less than or equal to entrance threshold signal strength 614, worker device 404 may detect an exit event. The monitoring device (e.g., worker device 404) may apply an event detection algorithm to compare the signal strength (RSSI) of exit signal 410 with entrance threshold signal strength 614.

In one embodiment, exit signal 410 may also be received by worker device 404 when worker device 404 exits an exit zone (e.g., exit zone 412). Exit zone 412 may be an area around entrance zone 406, and may account for worker device 404 entering and exiting entrance zone 406 multiple times. Exit zone 412 may also be a patient zone. For example, and referring to FIG. 4b, if an employee (e.g., a nurse) is caring for a patient, the nurse may move in and out of entrance zone 406. The nurse may give the patient medication, which may require the nurse to move into entrance zone 406. The nurse may also tend to medical device 414, which may be just outside entrance zone 406 and may require the nurse to move outside entrance zone 406. Further, the nurse may be required to adjust hypodermic needle 416 of intravenous system 418, which may require the nurse to again move into entrance zone 406. Receiving exit signal 410 when the nurse leaves exit zone 412 may account for the multiple entrances and exits of the nurse into entrance zone 406 during a relatively short period of time. Compliance device 408 may be configured to transmit exit signal 410 when worker device 404 exits entrance zone 406 or exit zone 412.

Further, in another example, exit zone 412 may also have an exit threshold signal strength. When worker device 404 receives a signal with an RSSI corresponding to the exit threshold signal strength, it may reset timer 616. The exit threshold signal strength may be lower than the entrance threshold signal strength. In other words, if worker device 404 receives a signal with an RSSI less than or equal to the entrance threshold signal strength, but greater than or equal to the exit threshold signal strength, it may reset timer 616. The monitoring device (e.g., worker device 404) may apply an event detection algorithm to compare the signal strength (RSSI) of the signal with the entrance threshold signal strength and the exit threshold signal strength. It should be noted that the entrance threshold signal strength and the exit threshold signal strength may be adjusted based on the relative proximity desired to associate the monitoring device with an enter or exit action. Timer 616 may then again count down the adjustable period of time, and may detect an exit event (e.g., exit event 624) when timer 616 expires. In this way, worker device 404 may account for multiple entrances and exits of the nurse into entrance zone 406 during a short period of time, as described above.

In another implementation, exit signal 410 may be received by worker device 404 when worker device 404 has not detected that it is in entrance zone 406 or exit zone 412 for a period of time. For example, once worker device 404 has entered and exited either entrance zone 406 or exit zone 412, and 180 seconds has passed without worker device 404 detecting that it is in exit zone 412, it may receive exit signal 410. This period of time may be adjustable. Exit zone 412 may have an adjustable radius, which may be configured to be a 12 foot radius.

Referring now to FIG. 10, in another embodiment, the monitoring device may set 1012 a current zone of the monitoring device (e.g., worker device 404) to a zone ID, which may be included in the enter signal. If another signal is received 1014 (e.g., from compliance device 408) with the same zone ID, and an RSSI greater than or equal to the exit threshold signal strength, the timer (e.g., timer 616) may be reset. In this way, worker device 404 may be informed that it is still in the patient zone with the zone ID, even though the timer has expired. Also, if, another signal is received 1016 (e.g., from compliance device 408) with a different zone ID than the patient zone, and an RSSI greater than or equal to an entrance threshold signal strength, an exit event may be recorded with worker device 404, the current zone of worker device 404 may be set to the new zone ID, and the timer may be reset. It should be noted that the entrance threshold signal strength may be one associated with a different patient zone with the different zone ID. In this way, worker device 404 may be informed that it is in a different patient zone even though the timer has not expired.

An action signal (e.g., signal 420) may be received 304 if an action device (e.g., action device 422) is actuated. Action signal 420 may be received by worker device 404 and may include an action status. Further, action signal 420 may be sent by action device 422. Action device 422 may be a device similar to monitoring device 10 and or remote device 126 and may also include, or be in communication with, a component configured to detect squeezing, pressure, motion, or other actions. Action device 422 may be affixed to a soap bottle (e.g., soap bottle 424), hand sanitizer dispenser, tap, faucet, glove dispenser, paper towel dispenser, and/or hand dryer. For example, a hand sanitizer bottle may include an elastomer sleeve, which may hold a component configured to detect squeezing. If the hand sanitizer bottle is squeezed by an employee (e.g., a nurse), the component may actuate (i.e., activate) action device 422. In response, action device 422 may, in turn, send action signal 420, which may be received by worker device 404.

If action device 422 is actuated, a monitoring device (e.g. worker device 404) may detect 1004 an action event 618 when the monitoring device (e.g., worker device 404) receives an action signal (e.g., action signal 620) with at least action threshold signal strength 622. Action threshold signal strength 622 may be associated with action device 422. In other words, when action event 618 is detected, the monitoring device (e.g., worker device 404) may be close enough to action device 422 such that the nurse wearing the monitoring device may be responsible for actuating action device 422. The monitoring device (e.g., worker device 404) may apply an event detection algorithm to compare the signal strength (RSSI) of the action signal 620 with action threshold signal strength 622. Action threshold signal strength 622 may be adjusted based on a relative proximity desired to associate worker device 404 with actuation of action device 422. Further, the monitoring device (e.g., worker device 404) may store action event 618 in its memory (e.g., flash memory 104) and/or may send an indication of action event 618 to computer 124.

In another example, soap bottle 424 may include or be in communication with a component to detect pressure, such as a pressure sensitive plate that detects pumping. If soap bottle 424 is pumped by an employee (e.g., a nurse) the component may actuate, (i.e., activate) action device 422. In response, action device 422 may, in turn, send action signal 420, which may be received by worker device 404. An action device included with a soap bottle or hand sanitizer bottle may be referred to herein as a "dispense device" and may be configured to transmit a dispense signal including a dispense status if the dispense device is actuated. The dispense signal and dispense status may be similar to the action signal and action status as referred to herein.

Referring now to FIG. 5, at least one of the enter status (e.g., enter status 502), exit status (e.g., exit status 512), and action status (e.g., action status 522) may include at least one of a date and time, a zone identification, an action device identification, and a compliance device identification. For example, enter status 502 may include date 504, time 506, zone identification (i.e., Zone ID) 508, and compliance device identification (i.e., Compliance Device ID) 510. Date 504 and time 506 may be a date and time that an employee (e.g., a nurse) entered an entrance zone (e.g., entrance zone 406). Zone ID 508 may identify a patient room where the entrance zone is located, or may be another area where medical error reduction is desired. Compliance Device ID 510 may identify a compliance device (e.g., compliance device 408) in a patient room, for example.

Similarly, exit status 512 may include date 514, time 516, zone identification (i.e., Zone ID) 518, and compliance device identification (i.e., Compliance Device ID) 520. Date 514 and time 516 may be a date and time that an employee (e.g., a nurse) exited an entrance zone (e.g., entrance zone 406).

Further, and as discussed above, date 514 and time 516 may be a date and time that an employee (e.g., a nurse) exited an exit zone (e.g., exit zone 412). Zone ID 518 may identify a patient room where the entrance zone is located, or may identify another area where medical error reduction is desired. Compliance Device ID 510 may identify a compliance device (e.g., compliance device 408) in a patient room, for example.

Action status 522 may include date 524, time 526, zone identification (i.e., Zone ID) 528, and compliance device identification (i.e., Compliance Device ID) 530. Date 524 and time 526 may be a date and time that an employee (e.g., a nurse) used a soap bottle (e.g., soap bottle 424) and, in turn, caused an action device (e.g., action device 424) to actuate. Zone ID 528 may identify a patient room where the action is located, or may be another area where medical error reduction is desired. Activity Device ID 530 may identify an activity device (e.g., action device 424) in a patient room, for example.

Enter status 502, exit status 512, and action status 522 may be included in enter signal 402, exit signal 410, and action signal 420, respectively. Each of enter signal 402, exit signal 410, and action signal 420 may comprise a number of pings including a number of packets (e.g., RF packets). Further, the packets may include values representing enter status 502, exit status 512, and action status 522, and the information shown for each in FIG. 5. It should be noted that the information in FIG. 5 is shown for illustrative purposes only, and the signals and statuses discussed above may include other information as well.

Referring now also to FIGS. 3 & 6*a*, at least one of enter status 502, exit status 512, and action status 522 may be sent 322 to a server computer (e.g., computer 124 shown in FIG. 1) or other computing device. The statuses may be sent to computer 124 by worker device 404. Computer 124 may be configured to receive at least one of enter status 502, exit status 512, and action status 522. Further, the presence of at least one of a compliance opportunity (e.g., compliance opportunity 602, 606) and a compliance action (e.g., compliance action 604) may be determined 306 based upon, at least in part, at least one of entrance status 502, exit status 512, and action status 522, or any information therein. Referring to FIGS. 6*b* & 10, the presence of at least one of a compliance opportunity (e.g., compliance opportunity 602, 606) and a compliance action (e.g., compliance action 604) may be determined 1008 based upon, at least in part, at least one of enter event 610, exit event 624, and action event 618. Compliance opportunities and compliance actions may be determined by the server computer (e.g., computer 124), by worker device 404 itself, or by another computing device configured to do so. In some implementations, worker device 404 may send the events and/or statuses to a base station, which may then send the statuses to the server computer.

An organization (e.g., a hospital) may require all employees (e.g., doctors, nurses, technicians, environmental services staff, transportation aides, volunteers, etc.) to wear a worker device. In this way, one or more base stations and/or server computers may collect statuses representing activity data for all employees in an organization (e.g., health-care workers in a hospital), 24 hours a day, 7 days a week. The activity data may be used to determine medical error reduction compliance statistics for each employee, for specific areas, or for the entire organization.

For example, if an employee (e.g., a nurse) moving around a hospital wearing worker device 404 entered entrance zone 406 at 05:22:34 PM, and exited entrance zone 406 at 05:28:12 PM, it may be determined that compliance opportunity 602 was created. Further, if the employee caused action device 422 of soap bottle 424 to be actuated at 05:28:46 PM, it may be determined that compliance action 604 occurred. A compliance opportunity may include, but is not limited to, an opportunity for an employee (e.g., a nurse) to clean his/her hands or otherwise perform a hand hygiene activity. A compliance action may include, but is not limited to washing and/or cleaning hands, or another hand hygiene activity.

Similarly, if the employee entered an entrance zone associated with laboratory 107 at 06:15:00 PM, and exited the entrance zone at 06:17:23 PM, it may be determined that compliance opportunity 606 was created. However, if the employee failed to cause an action device associated with laboratory 107 to be actuated, it may be determined that the employee failed to take a compliance action. In this way, at least one of compliance opportunity 602 and compliance action 604 may be determined based upon, at least in part, at least one of the date (e.g., date 504, 514, 524) and time (e.g., time 506, 516, 526), the zone identification (e.g., Zone ID 508, 518, 528), the action device identification (e.g., Activity Device ID 530) and the compliance device identification (e.g., Compliance Device ID 510, 520). At least one of the first worker device, the action device, compliance device, and the server computer may be configured to determine the presence of at least one of a compliance opportunity and a compliance action, based upon, at least in part, at least one of the enter status, the exit status, and the action status. It should be noted that the various devices described herein may each be configured to transfer status information between one another. In this way, any of the devices described herein may receive signals including statuses of other devices, and other status information in order to perform operations described herein, such as determine the presence of at least one of a compliance opportunity and a compliance action.

In some implementations, an adherence (e.g., adherence rate 608) may be calculated 308 (1010) based upon, at least in part, the at least one compliance opportunity (e.g., compliance opportunity 602) and compliance action (e.g., compliance action 604). Adherence rate 608 may be the total number of compliance actions divided by the total number of compliance opportunities. Adherence rate 608 may be calculated based upon compliance actions and compliance opportunities for a given date/time period, specific zone and/or location, specific worker device, specific employee, or a combination thereof. For example, adherence rate 608 may be calculated for all zones in an entire hospital for an entire month. In another example, and as shown in FIG. 6, adherence rate 608 may be calculated for worker device 404 (which may be associated with a certain employee), and for the date/time period Dec. 13, 2009 between 05:00:00 PM and 07:00:00 PM. With one compliance action (e.g., compliance action 604) and two compliance opportunities (e.g., compliance opportunities 602, 606), the calculation may be ½=0.5. The calculation may also be multiplied by 100%, leaving a 50% adherence rate (e.g., adherence rate 608). At least one of the first worker device, the action device, compliance device, and the server computer may be configured to calculate an adherence rate based upon, at least in part, the at least one compliance opportunity and compliance action.

Referring back to FIGS. 2 & 3, a proximity (e.g., proximity 224) may be calculated 310 between first worker device 218 and at least one of a compliance device (e.g., compliance device 408) and second worker device 222. Proximity 224 may be calculated based upon, at least in part, information in signals exchanged between first worker device 218 and second worker device 222. These signals may include a worker device status, which may include a worker device identification, date, and time. If proximity 224 is less than an adjustable distance, first and second worker devices 218 and 222 may determine that a face-to-face contact has occurred between employees wearing the worker devices. Face-to-face contact may signify a compliance opportunity. At least one of the first worker device, the second worker device, and the compliance device may be configured to calculate a proximity between the first worker device and the compliance device. In one embodiment, proximity may be calculated based upon the signal strength of the signals exchanged between the first and second worker devices.

Further, zone 226 may be determined 312 based upon, at least in part, proximity 224. Zone 226 may represent an area around worker devices 218 and 222. Employees wearing first and second worker devices 218 and 222 may enter and exit zone 226, and this may create a compliance opportunity. Further, zone 228 may also be determined based upon, at least in part, at least one of proximity 224 and zone 226. Zones 226 and 228 may be used to determine the presence of a compliance opportunity. For example, an entrance signal may be received by second worker device 222 when second worker device 222 enters zone 226. The entrance signal may be sent by first worker device 228 and may include an entrance status. A first exit signal may be received by second worker device 222 when second worker device 222 exits zone 226 and may include a first exit status. The first exit signal may be sent by first worker device 218 and may include a first exit status. In some embodiments, a second exit signal may be received by second worker device 222 when second worker device 222 exits zone 228. Zone 228 may be an area around zone 226, and may account for second worker device 222 entering and exiting zone 226 multiple times. For example if an employee wearing second worker device 222 interacts with an employee wearing first worker device 218 in the hall way of a hospital, the employees may move around each other and may cause first and second worker devices 218 and 222 to move in and out of zone 226 multiple times. Receiving the second exit signal when second worker device 222 exits zone 228 may account for multiple entrances and exits of the employees into and out of zone 226 during a relatively short period of time. At least one of the first worker device, the second worker device, and the compliance device may be configured to determine zone 226 and/or zone 228 based upon, at least in part, proximity 224. Zone 226 and/or zone 228 may also be determined by the signal strength of signals exchanged between the first and second worker devices.

Figure 7:
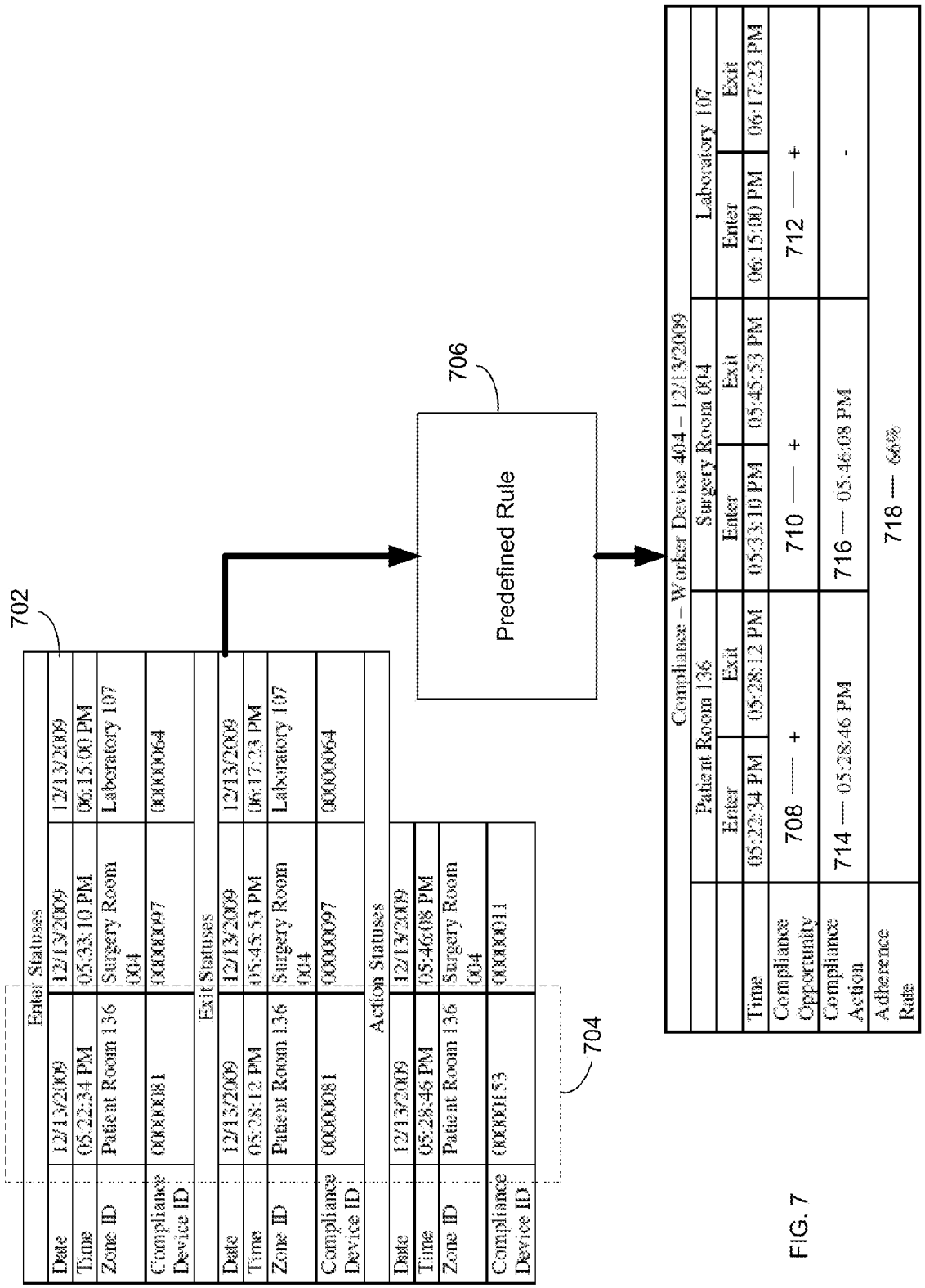
FIG. 7 is diagrammatic flowchart showing calculation of an adherence rate for medical error reduction.

Referring to FIGS. 3 & 7, a plurality of enter statutes, exit statuses, and action statuses (e.g., plurality of statuses 702) may be aggregated 314 into a time-based sequence of events (e.g., sequence of events 704). Plurality of statuses 702 may be included in a plurality of enter signals, exit signals, and action signals, which may be received by one or more worker devices worn by one or more employees. Plurality of statuses 702 may also be sent to a server computer, and may be aggregated therein. At least one of the first worker device, the action device, compliance device, and the server computer may be configured to aggregate the plurality of enter statuses, exit statuses, and action statuses into the time-based sequence of events. Also, a plurality of enter events, exit events, and action events may be aggregated into a time-based sequence of events (e.g., sequence of events 704).

Sequence of events 704 may be run 316 through at least one predefined rule (e.g., predefined rule 706). The presence of at least one of a compliance opportunity (e.g., compliance opportunity 708, 710, 712) and compliance action (e.g., compliance action 714, 716) may be determined 318 based upon, at least in part, the sequence of events (e.g., sequence of events 704) and the at least one predefined rule (e.g., predefined rule 706). Predefined rule 706 may be an algorithm reflecting a workplace policy on compliance actions, such as hand hygiene. The algorithm may reflect various policies, including the amount of time a nurse may be in a patient room before a compliance opportunity occurs. At least one of the first worker device, the action device, compliance device, and the server computer may be configured to run the sequence through the at least one predefined rule and/or determine the presence of least one of the compliance opportunity and compliance action based upon, at least in part, the sequence and the at least one predefined rule.

For example, compliance opportunities may be determined according to the World Health Organization's (WHO) policies for hand hygiene. The WHO recommends that healthcare workers (e.g., nurses, or others that may wear worker devices) clean their hands when the following "moments" occur: (i) before touching patients, (ii) before clean/aseptic procedures, (iii) after body fluid exposure/risk, (iv) after touching a patient, and (v) after touching patient surroundings. The medical error reduction process and/or devices discussed herein may be configured to determine these moments based upon signals and status information exchanged by the devices. These moments may be determined by the predefined rule, and may count as compliance opportunities.

Referring now to FIG. 11, a compliance opportunity may be determined based upon, at least in part, a probability of contact (e.g., probability 1202). Further, the probability of contact may be retrieved from a lookup table (e.g., table 1200). As discussed above, WHO's moments (i), (iv), and (v) may be before touching a patient, after touching a patient, and after touching patient surroundings (e.g., bed linens, pillows, patient gowns) respectively. In one implementation, enter events and exit events, and their respective statuses, may be used to determine a probability of contact with a patient. Based upon the probability of contact, an enter event and exit event may be categorized as "before patient contact" and "after patient contact", respectively. Information from enter and exit statuses, including but not limited to time of day the status was recorded (e.g. time 1204), role of the badge wearer (i.e., nurse, physical therapist, doctor, visitor), type of patient zone (e.g., private room, semi-private room, bed in multi-bed ward, patient-worn beacon), and the hospital where the patient zone is located may be used to determine the probability of patient contact, which may further be used to determine if the enter event and/or exit event can be categorized as a WHO moment. The probability of patient contact may also be used as a weighting factor when calculating an average compliance rate across events.

For example, a probability of contact of 89% (e.g., probability of contact 1202) may be determined based upon, at least in part, an event duration (e.g., event duration or Log 10 duration 1208) and time 1204. Event duration 1208 may be an amount of time between an enter event and an exit event. If probability of contact 1202 is greater than a threshold probability (e.g., 80%), it may be determined that the enter event and the exit event are categorized as "before patient contact" and "after patient contact". The "before patient contact" and "after patient contact" may be used, with the probability, to determine whether or not there is a compliance opportunity, or to make subsequent determinations and/or calculations.

As discussed above, probability of contact 1202 may be retrieved from table 1200, which may be a lookup table. Values in the table may be pre-computed from observational data, heuristics, and other means. The threshold probability may be adjustable. The table may be indexed by hour of day of the enter and/or exit event, and duration between the enter and exit events. While table 1200 shows a probability scale (e.g., scale 1206) which increases from lighter to darker shade and/or color, other variations may be used.

In another example, predefined rule 706 may include one or more of the following algorithms to determine medical error. If status information shows that a worker device has (i) exited a patient zone, (ii) detected no compliance action, and (iii) entered another patient zone, it may be determined that the employee wearing the worker device failed to take a compliance action, which may signify medical error. If status information shows that a worker device has (i) exited a patient zone, and (ii) detected no compliance action for 2 minutes, it may be determined that the employee wearing the worker device failed to take a compliance action, again signifying medical error. This amount of time may be configurable, based upon the organization's (e.g., a hospital) policy. Similarly, if status information shows that a worker device has (i) detected no compliance action for 2 minutes, and (ii) entered a patient zone, it may be determined that the employee wearing the worker device failed to take a compliance action, also signifying medical error. Further, if status information shows (i) a first nurse wearing a first worker device enters a hospital or unit of the hospital, (ii) the first nurse wearing the first worker device has face-to-face contact with a second nurse wearing a second worker device, (iii) the second nurse leaves the hospital or unit of the hospital, and (iv) no compliance action is detected, it may be determined that the second nurse failed to take a compliance action, further signifying medical error.

An adherence rate (e.g., adherence rate 718) may be calculated 320 based upon, at least in part, the at least one compliance opportunity (e.g., compliance opportunity 708, 710, 712) and compliance action (e.g., compliance action 714, 716). Adherence rate 718 may be the total number of compliance actions divided by the total number of compliance opportunities. With two compliance actions (e.g., compliance actions 714, 716) and three compliance opportunities (e.g., compliance opportunities 708, 710, 712), the calculation may be $2/3=0.66$. The calculation may also be multiplied by 100%, leaving a 66% adherence rate (e.g., adherence rate 718). At least one of the first worker device, the action device, compliance device, and the server computer may be configured to calculate the adherence rate based upon, at least in part, the at least one compliance opportunity and compliance action.

Compliance opportunities and compliance actions may be used to find medical error, or failure to take a compliance action. Compliance opportunities, compliance actions, medical errors, and adherence rates may be recorded in electronic medical record systems, and/or reported to the employee wearing the badge, to supervisors, and/or to hospital administrators. For example, on-demand hand hygiene compliance reporting may be derived from data collected on an individual level. Individual reporting may give administrators a scoring on how well particular healthcare workers are complying with hand hygiene policy. Location reporting may highlight trouble areas where hand hygiene setup may need to be adjusted. Category reporting may be used to compare compliance by role, department, shift or any other defined category. Further individual reporting may allow healthcare workers to know that they may be evaluated on their own compliance and not lumped together as an average.

Worker devices may also be worn by patients and/or visitors, and may also be referred to as patient devices and/or visitor devices. As such, the terms worker device, patient device, and/or visitor device may be used interchangeable to refer to a monitoring device worn by workers, patients, and/or visitors, respectively. In one embodiment, patients may wear patient devices in lieu of having beacon devices in patient rooms, and patient devices may transmit enter, exit, and action signals to worker devices. Additionally, any of the monitoring devices discussed herein (e.g., worker devices, patient devices, visitor devices) may have output capability and may notify the person wearing the device (e.g., employees such as nurses, patients, visitors, or others) that they are out of compliance. For example, the monitoring devices may include a vibration motor or buzzer which vibrates when the worker is out of compliance, or a speaker to output an alarm when the worker is out of compliance. As discussed above, the monitoring devices may also include an LED which may indicate when the worker is out of compliance.

Figure 8:
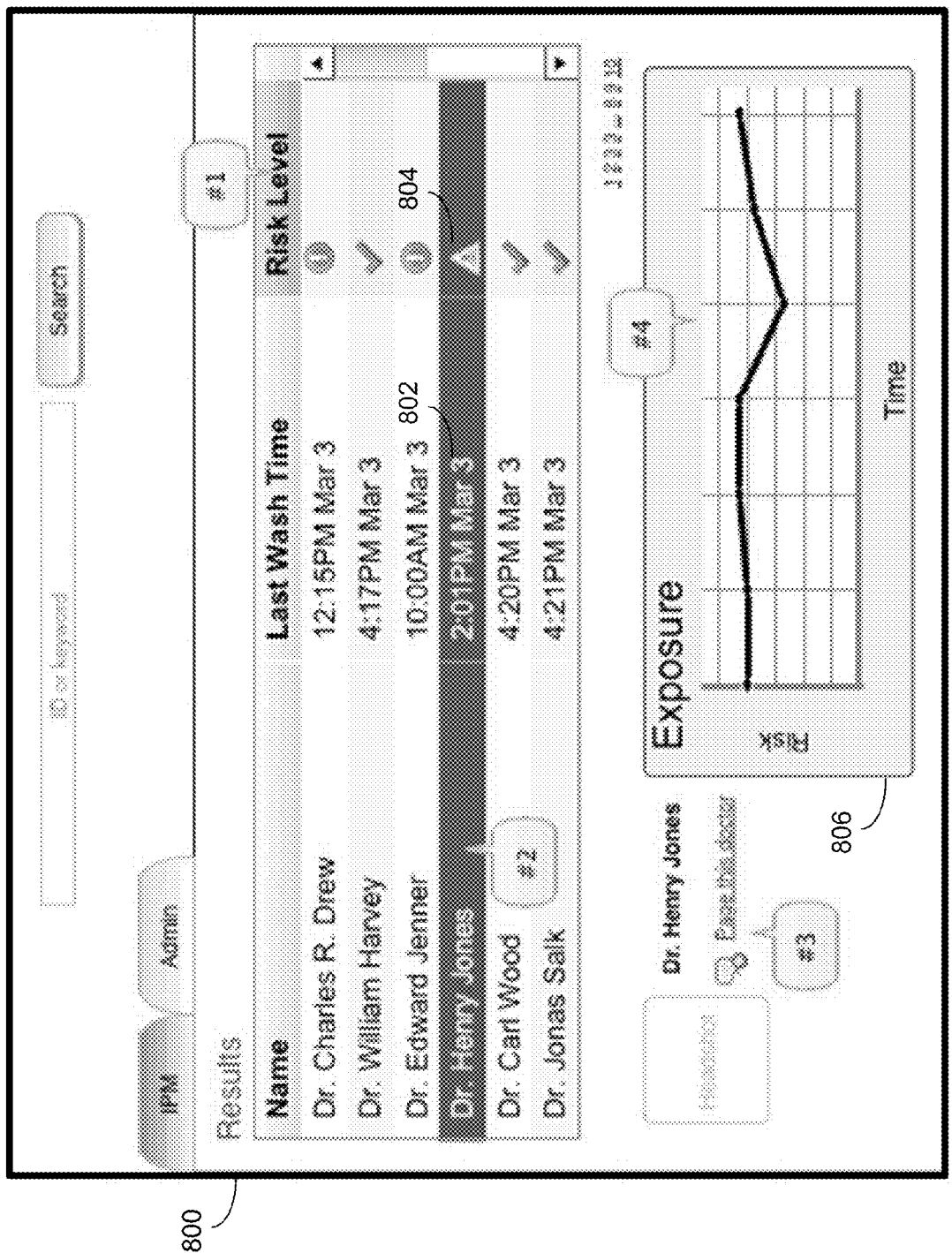
FIG. 8 is a webpage which may be displayed during the medical error reduction process.
Figure 9:
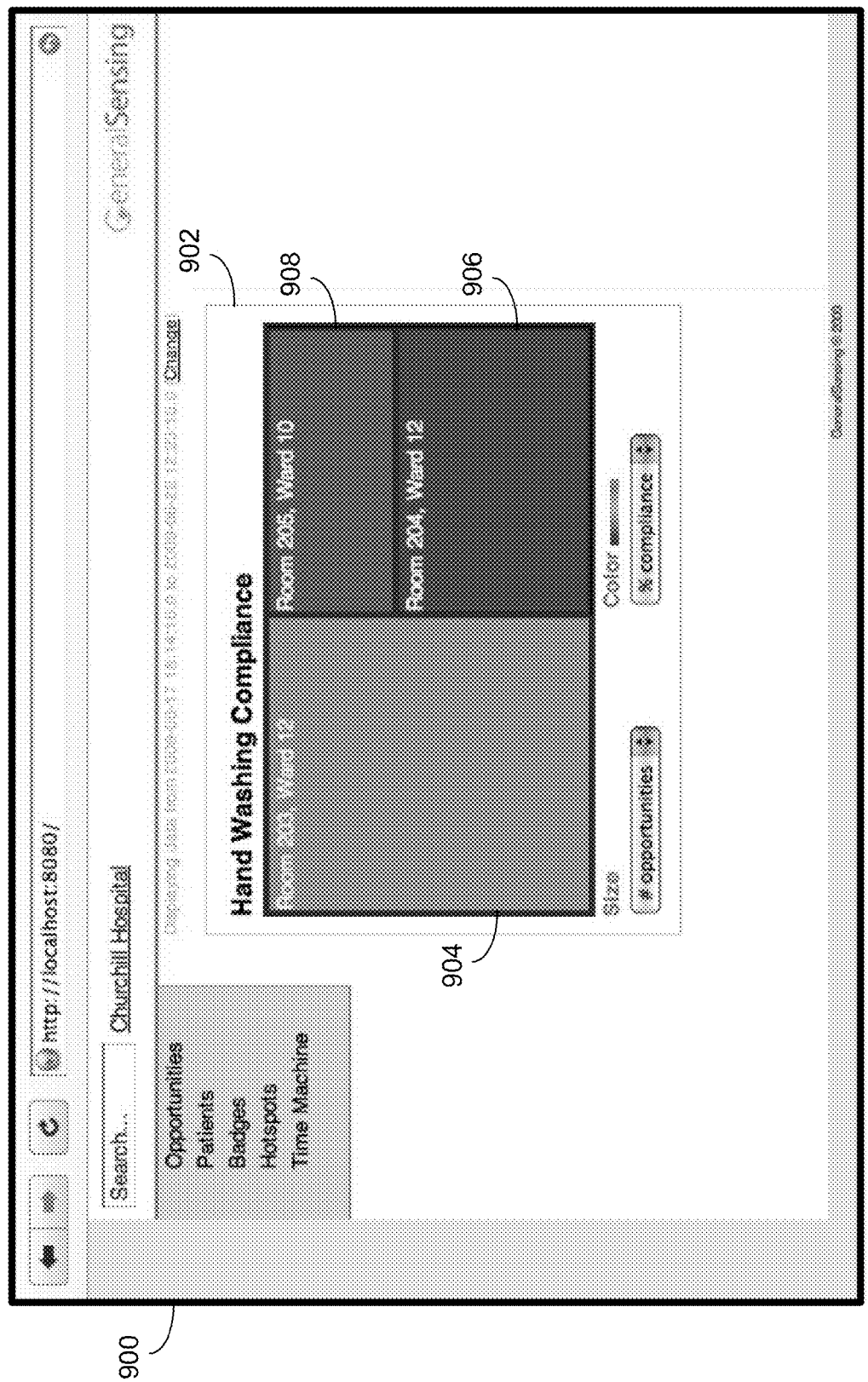
FIG. 9 is a webpage which may be displayed during the medical error reduction process.

The statuses, data, and analysis determined may be reported in a number of ways, including but not limited to, displaying such information on a computer display or over a webpage. For example, and as shown in FIG. 8, a webpage (e.g., webpage 800) may show data regarding individual employees such as doctors, for example. Last wash time 802 may be shown in the webpage and may be determined based upon various statuses received by a worker device worn by the doctor. Further, risk level 804 may be determined by pre-defined rule 706 based upon, at least in part, last wash time 802. Selection of a certain doctor on the webpage may cause the webpage to render chart 806, which may show a graph of the risk created by the doctor over time based upon, at least in part, the wash times (e.g., compliance actions) recorded by the doctor's worker device.

In some implementations, a webpage (e.g., webpage 900) may show compliance data regarding specific areas or rooms of an organization (e.g., a hospital). Webpage 900 may provide tools to identify compliance problems and to support behavior change programs. For example, webpage 900 may include a color-coded diagram (e.g., diagram 902) showing medical error reduction compliance levels of specific areas or rooms. Diagram 902 may include, for example, a green area (e.g., area 904) indicating a high percentage of compliance for that area (i.e., Room 203, Ward 12). Diagram 902 may further show a red area (e.g., area 906) indicating a low percentage of compliance for that area (i.e., Room 204, Ward 12). Diagram 902 may also show a dark red area (e.g., area 908) indicating an extremely low level of compliance for that area (i.e., Room 205, Ward 10). The tools provided by webpage 900 may show various areas based upon the number of compliance opportunities recorded and/or the number of compliance actions recorded.

Some of the features described above, including but not limited to determinations and calculations, may be implemented as software modules executed by a processor of a computing system, and/or in a computer program product that may be stored on a storage device, storage medium, or computer readable medium having instructions that when executed by a processor perform portions of the discovery process above. The storage device, storage medium, or computer readable medium may include, but is not limited to, any type of disk including floppy disks, optical disks, compact disk read only memories (CD-ROMS), compact disk rewritables (CD-RWs), magneto-optical disks, semiconductor devices such as read-only memories (ROMs), random access memories (RAMs) such as dynamic and static RAMs, electronically erasable programmable read-only memories (EE-PROMs), flash memories, magnetic or optical cards, or any type of media suitable for storing electronic instructions. Other embodiments may be implemented as software modules executed by a programmable control device.

The flowchart and block diagrams in the figures may illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Further, one or more blocks shown in the block diagrams and/or flowchart illustration may not be performed in some implementations or may not be required in some implementations. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

A number of implementations have been described. Nevertheless, it will be understood that various modifications may be made. Accordingly, other implementations are within the scope of the following claims.

What is claimed is:

1. A method for reducing medical error comprising:
receiving an enter signal including an enter status using a first worker device entering a zone, the first worker device being a body-worn device worn by a human, the enter signal received by the first worker device;
receiving an exit signal including an exit status using the first worker device exiting an additional zone including an area around the zone, the exit signal received by the first worker device; and
receiving an action signal including an action status using the first worker device in response to an action device is actuated, the action signal received by the first worker device,
wherein the enter signal has a strength of at least an entrance threshold signal strength associated with the zone, and the exit signal has a strength less than or equal to the entrance threshold signal strength but greater than or equal an exit threshold signal strength associated with the additional zone.

2. A method for reducing medical error comprising:
receiving an enter signal including an enter status using a first worker device entering a zone, the first worker device being a body-worn device worn by a human;
receiving an exit signal using the first worker device exiting an additional zone including an area around the zone; and
receiving an action signal including an action status using the first worker device in response to an action device is actuated,
wherein the enter signal has a strength of at least an entrance threshold signal strength associated with the zone, and the exit signal has a strength less than or equal to the entrance threshold signal strength but greater than or equal an exit threshold signal strength associated with the additional zone.

3. The method of claim 2 further comprising:
determining the presence of at least one of a compliance opportunity and a compliance action using the first worker device, based upon, at least in part, at least one of the enter status, the exit status, and the action status.

4. The method of claim 2 further comprising:
sending at least one of the enter status, the exit status, and the action status from the first worker device to a server computer.

5. The method of claim 2 further comprising:
calculating a proximity between the first worker device and a second worker device being another body-worn device worn by another human; and
determining the zone based upon, at least in part, the proximity.

6. The method of claim 3 further comprising:
calculating an adherence rate based upon, at least m part, the at least one compliance opportunity and compliance action.

7. The method of claim 2 wherein at least one of the enter status, the exit status, and the action status include at least one of a date and time, a zone identification, an action device identification, and a compliance device identification.

8. The method of claim 7 wherein at least one of the compliance opportunity and compliance action are determined based upon, at least one of the date and time, the zone identification, the action device identification, and the compliance device identification.

9. The method of claim 2 further comprising:
aggregating a plurality of enter statuses, exit statuses, and action statuses into a time-based sequence of events;
running the sequence through at least one predefined rule;
determining the presence of at least one of a compliance opportunity and compliance action based upon, at least in part, the sequence and the at least one predefined rule; and
calculating an adherence rate based upon, at least in part, the at least one compliance opportunity and compliance action.

10. An apparatus for reducing medical error comprising:
a first worker device being a body-worn device configured to be worn by a human and receive an enter signal including an enter status when the first worker device enters a zone, an exit signal including an exit status when the first worker device exits an additional zone including an area around the zone, and an action signal including an action status if an action device is actuated, wherein the enter signal has a strength of at least an entrance threshold signal strength associated with the zone, and the exit signal has a strength less than or equal to the entrance threshold signal strength but greater than or equal an exit threshold signal strength associated with the additional zone.

11. The apparatus of claim 10 wherein the first worker device is further configured to determine the presence of at least one of a compliance opportunity and a compliance action, based upon, at least in part, at least one of the enter status, the exit status, and the action status.

12. The apparatus of claim 10 wherein the first worker device is further configured to:
send at least one of the enter status, the exit status, and the action status to a server computer.

13. The apparatus of claim 10 wherein the first worker device is further configured to:
calculate a proximity between the first worker device and a second worker device being another body-worn device configured to be worn by another human; and
determine the zone based upon, at least in part, the proximity.

14. A system for reducing medical error comprising:
a first worker device being a body-worn device configured to be worn by a human and receive:
an enter signal including an enter status when the first worker device enters a zone;
an exit signal including an exit status when the first worker device exits an additional zone including an area around the zone; and
an action signal including an action status if an action device is actuated; and
the action device configured to transmit the action signal including the action status if the action device is actuated,
wherein the enter signal has a strength of at least an entrance threshold signal strength associated with the zone, and the exit signal has a strength less than or equal to the entrance threshold signal strength but greater than or equal an exit threshold signal strength associated with the additional zone.

15. The system of claim 14 further comprising:
a compliance device configured to:
transmit the enter signal including the enter status when the first worker device enters the zone; and
transmit the exit signal including the exit status when the first worker device exits the zone.

16. The system of claim 15 further comprising:
a server computer configured to receive at least one of the enter status, the exit status, and the action status.

17. The system of claim 16 wherein the first worker device is further configured to determine the presence of at least one of a compliance opportunity and a compliance action, based upon, at least in part, at least one of the enter status, the exit status, and the action status.

18. The system of claim 17 wherein at least one of the first worker device, the action device, compliance device, and the server computer are configured to calculate an adherence rate based upon, at least in part, the at least one compliance opportunity and compliance action.

19. The system of claim 15 wherein at least one of the first worker device and the compliance device are further configured to:
calculate a proximity between the first worker device and the compliance device; and
determine the zone based upon, at least in part, the proximity.

20. The system of claim 14 further comprising:
a second worker device being another body-worn device configured to be worn by another human, and wherein at least one of the first worker device and the second worker device is further configured to:
calculate a proximity between the first worker device and the second worker device; and
determine the zone based upon, at least in part, the proximity.

21. The system of claim 14 wherein at least one of the enter status, the exit status, and the action status include at least one of a date and time, a zone identification, an action device identification, and a compliance device identification.

22. The system of claim 16 wherein at least one of the first worker device, the action device, compliance device, and the server computer are configured to:
aggregate a plurality of enter statuses, exit statuses, and action statuses into a time-based sequence of events;
run the sequence through at least one predefined rule;

determine the presence of the at least one of a compliance opportunity and compliance action based upon, at least in part, the sequence and the at least one predefined rule; and calculate an adherence rate based upon, at least in part, the at least one compliance opportunity and compliance action.

23. A hand hygiene system for reducing medical error comprising:
- a beacon device configured to be in a patient zone and transmit:
  - an enter signal including an enter status when a body-worn device enters the patient zone; and
  - an exit signal including an exit status when the body-worn device exits an additional zone including an area around the patient zone;
- a dispense device configured to transmit a dispense signal including a dispense status if the dispense device is actuated; and
- the body-worn device configured to be worn by a human, receive the enter signal, the exit signal, and the dispense signal, and determine the presence of a compliance opportunity and a compliance action based upon the enter status, the exit status, and the action status, wherein the enter signal has a strength of at least an entrance threshold signal strength associated with the patient zone, and the exit signal has a strength less than or equal to the entrance threshold signal strength but greater than or equal an exit threshold signal strength associated with the additional zone.

24. A method for reducing medical error comprising:
- detecting an enter event when a monitoring device receives an enter signal with at least an entrance threshold signal strength associated with a zone, the monitoring device being a body-worn device configured to be worn by a human;
- setting a timer associated with the zone;
- resetting the timer when the monitoring device receives a signal with a signal strength less than or equal to the entrance threshold signal strength but greater than or equal to an exit threshold signal strength, the exit threshold signal strength lower than the entrance threshold signal strength;
- if an action device is actuated, detecting an action event when the monitoring device receives an action signal with at least an action threshold signal strength; and
- detecting an exit event when the timer expires.

25. The method of claim 24 further comprising:
- determining the presence of at least one of a compliance opportunity and a compliance action using the monitoring device, based upon, at least in part, at least one of the enter event, the exit event, and the action event.

26. The method of claim 25 further comprising:
- calculating an adherence rate based upon, at least in part, the at least one compliance opportunity and compliance action.

27. The method of claim 25 wherein the compliance opportunity is determined based upon, at least in part, a probability of contact.

28. The method of claim 27 wherein the probability of contact is retrieved from a lookup table.

* * * * *